United States Patent [19]

Petersen

[11] 4,105,628
[45] Aug. 8, 1978

[54] HALOGEN-CONTAINING AROMATIC ETHER-ESTER FIRE-RETARDANTS FOR PLASTICS

[75] Inventor: Egon Norbert Petersen, Neunkirchen-Seelscheid, Fed. Rep. of Germany

[73] Assignee: Dynamit Nobel Aktiengesellschaft, Troisdorf, Fed. Rep. of Germany Germany

[21] Appl. No.: 728,097

[22] Filed: Sep. 30, 1976

[30] Foreign Application Priority Data

Oct. 4, 1975 [DE] Fed. Rep. of Germany ....... 2544513

[51] Int. Cl.² .................. C07C 69/76; C08K 5/41; C08K 5/10; C08K 5/36
[52] U.S. Cl. .................. 260/45.85 R; 560/65; 260/455 R
[58] Field of Search .............. 260/473 R, 45.85; 71/108; 560/65

[56] References Cited

U.S. PATENT DOCUMENTS 3,609,167 9/1971 Zirkle ............................. 260/473
3,956,399 5/1976 Paritee et al. ..................... 260/45.85
3,983,164 9/1976 Thorne et al. .................... 260/473 R

*Primary Examiner*—V. P. Hoke
*Attorney, Agent, or Firm*—Burgess, Dinklage & Sprung

[57] ABSTRACT

Aryloxymethylbenzoic acid phenyl ester of the formula

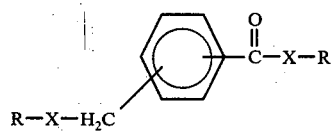

wherein X represents oxygen or sulfur, and each R represents residue of a mononuclear or polynuclear phenol which can be substituted. The ester can be produced by reacting the corresponding chloromethylbenzoic acid phenyl ester with the alkali salt of the phenol corresponding to the aryl group of said aryloxymethyl group. The products are useful as additives for plastics to impart flame resistance thereto.

12 Claims, No Drawings

HALOGEN-CONTAINING AROMATIC ETHER-ESTER FIRE-RETARDANTS FOR PLASTICS

BACKGROUND

The present invention relates to the preparation of novel aromatic compounds halogenated in the nucleus and containing both ether and ester groups, which are derived from the General Formula I, and to these compounds themselves.

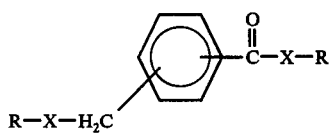

I

The subject matter of the invention, therefore, is the three isometric o-, m- and p-haloaryloxymethyl (or -mercaptomethyl)benzoic acid halophenyl esters and thiohalophenyl esters of Formula I, wherein X can represent oxgyen or sulfur and the X's can be the same or different.

If the ester group contains sulfur, the compounds of Formula I can also be referred to as substituted thiobenzoic acid-S-aryl esters.

R represents the residue of a mononuclear or polynuclear, halogen-substituted compound, which can include the substituent

The moiety R can be unsubstituted, or it may have substituents, especially halogen, e.g. chlorine and/or bromine atoms. The number of halogen atoms per aromatic ring preferably being from 2 to 5. The R's can be alike or different.

Especially the benzene ring is to be the basis of the nuclear rings, but other aromatic rings and heterocyclic rings are possible.

In the case of noncondensed polynuclear rings, the diphenyl radical is preferred among the nuclei joined by a single bond, while in the case of the rings joined by atom groups, benzene nuclei are preferred, the preferred connecting links being hydrocarbon moieties, such as a methylene group or a dialkylmethylene group, a chalcogen atom, such as an oxygen or sulfur atom, or the group -SO -, and still others are possible.

These polynuclear moieties are thus derived from the general formula

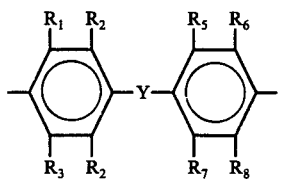

wherein the connecting link Y has the meaning given above and $R_1$ to $R_8$ represent hydrogen or halogen, the moieties $R_1$ to $R_8$ being able to be identical to one another or different.

Additional subject matter of the invention is a method for the preparation of the compounds of Formula I, which is characterized in that o-, m- or p-chloromethylbenzoic acid esters of halogenated phenols and/or thiophenols being monovalent or polyvalent, mononuclear or polynuclear, and alkali salts of unsubstituted or halogen-substituted phenols, or of the thiophenols corresponding thereto, are reacted with one another in appropriate solvents at elevated temperature.

The chlormethylbenzoic acid esters of phenols or thiophenols which are used as starting materials are easily obtainable substances whose preparation is described in German Patent Application P 24 47 385.6. (U.S. Pat. Ser. No. 619,351, filed Oct. 3, 1975, now abandoned and replaced by Ser. No. 804,837, filed June 8, 1977.)

The process is generally performed by placing the isomeric chloromethylbenzoic acid or chlormethylthiobenzoic acid halophenyl ester used as starting solution into a solution or suspension of an alkali salt of a (halo)-phenol or (halo)thiophenol in an inert solvent or reaction medium, and bringing this mixture to reaction at elevated temperature, with stirring. The ether-esters of the invention which are thus formed precipitate, as a rule, and are easily isolated, for example by suction filtering the cooled reaction mixture. The sodium chloride formed in the preparation reaction is removed from the ether-esters, and then the reaction product is dried in a conventional manner. The ether-esters of Formula I are obtained by the method of the present invention in a high yield and in good purity.

The alkali phenolates of the First Main Group of the Periodic System can be used as alkali salts of the (halo)-phenols, preferably the sodium and/or potassium phenolates.

It is a special feature of the present process that the alkali phenolates are prepared in situ in the solvent from the phenols and the particular alkali hydroxide or from the solutions thereof, which permits an especially economical procedure.

Suitable reaction media for the performance of the reaction of the process of the invention are the solvents or suspension media which are known in ester formation of phenol ether formation processes and are inert in the said processes, such as, for example, hydrocarbons, including xylene, ethers, such as dioxane, sulfoxides, such as dimethylsufoxide, but especially alkyleneglycolmonoalkyl ethers on account of their good dissolving ability with regard to the alkali phenolates to be used in accordance with the invention. Ethyleneglycol monomethyl ether, hereinafter referred to simply as methyl glycol, is used to special advantage in the performance of the process of the invention.

However, even other representatives of this group of solvents can be used with similar good success, such as for example, ethyleneglycol monoethyl ether, ethyleneglycol monobutyl ether, 1,4-butyleneglycol monomethyl ether, 1,4-butyleneglycol monoethyl ether, and others.

The reaction components are subjected to the reaction in equal molar ratios, as a rule, although a slight excess amounting, for example, to 10% by weight of chloromethylbenzoic acid ester, can be used.

One very especially advantageous variant of the present process is to set out, not from the chloromethyl(thio)benzoic acid esters, but from the o-, m- and/or p-chloromethylbenzoyl chloride, which is capable of yielding the new compounds of Formula I directly in a one-vessel process. In this one-vessel reaction procedure, the alkali phenolates can also be formed *in situ*. In this embodiment the ester is formed *in situ* and is then reacted to form the ether-ester.

The temperature range in which the process of the present invention can be performed with especial success has been found to be from +10° to 150° C, preferably from 25° to 130° C. In the case of the one-vessel reaction for the preliminary ester formation, a temperature from 10 to about 40° C is desirable.

The new substances of Formula I in accordance with the invention are effective and advantageous fire-retardant agents for plastics, e.g. synthetic plastics, such as, for example, polyolefins or polystyrene, acrylonitrile-butadiene-styrene polymers, polyesters, and numerous others.

Polyolefins, in the meaning of the present invention, are polyethylene of high or low density, polypropylene, polybutylene, polymethylpentene, and others.

The substances of the invention comply to a high degree with the requirements which must be met by a fire-retardant agent, and therefore another subject of this invention consists in the use of the ether-esters of Formula I as fire-retardant agents in plastics, as well as in these fire-retardant plastics themselves.

The ether-esters of the invention can easily be incorporated into plastics; they are well compatible with the polymers, as a rule they do not chalk out, and they are entirely stable at the required fabrication temperatures.

Another advantage of the substances of the invention is that relatively small amounts suffice for the achievment of good fire-retardancy, resulting in only minor alterations of the mechanical and physical properties of the finished products.

Still another advantage is that the halogen content of the substances of Formula I does not need to be as high as it does in many of the conventional fire-retardant agents known heretofore. Surprisingly, ether-esters of the invention having bromine contents of only 40 to 50 wt.-% have a good, and in some cases even equally good or better fire-retardant action as known compounds of higher degrees of bromination. Since the amount of bromine is an important cost factor in fire-retardant agents, comparatively low bromine contents present a technical and economical advantage.

The substances of the present invention are used in the polymers together with synergistic compounds such as zinc borate, sodium antimonite and, to special advantage, antimony trioxide.

In general, the fire-retardant agents of the invention are added in amounts of 2 to 15 wt.-%, preferably 3 to 10 wt.-%. Of the antimony trioxide, from 0.5 to 8 wt.-% is used, and, to special advantage, from 1 to 5 wt.-% with respect to the total amount of the plastic.

The incorporation of the fire-retardant additives can be accomplished in a conventional manner by mixing on heated rolls, mix-extruding, or other appropriate method. In addition, the adjuvant additives required in any particular case can be incorporated, such as, for example, lubricants, stabilizers, pigments, or other conventional additives.

EXAMPLES

The following examples are intended to explain the invention and the procedure thereof, without limiting same.

EXAMPLE 1

Preparation of o-(2,4,6-tribromophenoxymethyl)-benzoicacid-(pentabromophenyl) ester

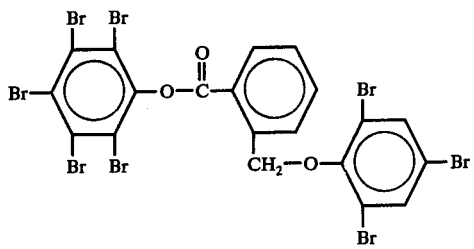

In a one-liter four-necked round flask equipped with stirrer, reflux condenser and thermometer, 4 g (= 0.1 mole) of solid sodium hydroxide was dissolved at 75° C in 1 liter of technical methyl glycol (B.P. 122°-126° C); then 33.08 g (= 0.1 mole) of tribromophenol was added, a clear solution being immediately obtained. Into this solution, at about 75° C, 64.15 g (= 0.1 mole) of o-chloromethylbenzoic acid pentabromophenyl ester was continuously stirred, and the mixture was heated with stirring at ebullition.

At approximately 120° C, the ether-ester that was formed began to precipitate in colorless form. To complete the reaction, refluxing was continued for one hour, with stirring; then the mixture was cooled to room temperature and the solids were separated by suction filtering.

The filter cake was washed first with methyl glycol, and then with water until the filtrate was free of chloride, and then it was dried.

We obtained 75.5 g of raw ether ester of the above structure, corresponding to a yield of 79.5% of the theoretically possible amount, melting point 246°-254° C.

10 g of the crude yield was recrystallized from 300 ml of xylene and yielded 8.4 g melting at 251°-254° C. Still another recrystallization yielded the analytically pure substance melting at 253°-255° C.

Elemental Analysis: $C_{20}H_8Br_8O_3$ (935.55) Calculated: C 25.68%, H 0.86%, O 5.13%, Br 68.33% Found: C 25.84%, H 0.77%, O 4.99%, Br 68.2%.

EXAMPLE 2

Preparation of m-(2,4,6-tribromophenoxymethyl)-benzoic acid-(pentabromophenyl) ester

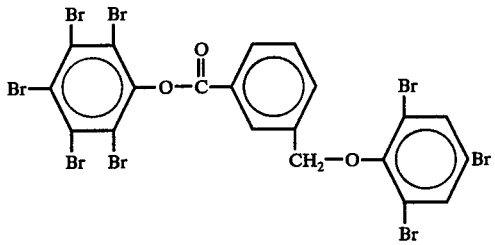

(a) M-Chloromethylbenzoic acid pentabromophenyl ester:

In a 500 ml flask equipped with stirrer, reflux condenser and thermometer,
350 ml of dry xylene, 244.4 g (= 0.5 mole) of pentabromophenol,
94.55 g (= 0.5 mole) of m-chloromethylbenzoyl chloride and
0.5 ml of anhydrous pyridine were combined and heated slowly, with stirring, in an oil bath. At approximately 100° C, the formation of hydrogen chloride began. The temperature of the mixture was slowly increased to the boiling temperature, and then, to complete the reaction, the mixture was refluxed for 7 hours, during which time a slow current of nitrogen was passed over the mixture. Then the mixture was cooled to room temperature, the contents of the flask solidifying to a colorless crystal mass, which was suction filtered, washed with xylene and dried at 80° C in vacuo.

Yield 270 g (= 84.2%), M.P. 154°-159° C; M.P. upon recrystallization 163°-165° C Elemental Analysis: $C_{14}H_6Br_5Cl\ O_2$ (641.20) Calculated: C 26.23%, H 0.94%, Br 62.32%, Cl 5.52%, O 4.99% Found: C 26.41%, H 0.81%, Br 62.4%, Cl 5.63%, O 5.11%

(b) m-(2,4,6-tribromophenoxymethyl)-benzoic acid-(pentabromophenyl) ester:

By the procedure described in Example 1,
600 ml of methyl glycol, B.P. 122-126
4 g (= 0.1 mole) of sodium hydroxide
33.1 g (= 0.1 mole) of tribromophenol and
64.15 g (= 0.1 mole) of the m-chloromethyl benzoic acid ester prepared in accordance with Example 2a, were reacted by refluxing for two hours, a portion of the ether ester that formed precipitating as soon as the boiling temperature was reached. After cooling to room temperature, the product was processed as described in Example 1.

76.7 g of the raw ether ester (82% yield) was obtained, which melted at 198°-205° C; upon recrystallization, the melting point was 205°-209° C Elemental Analysis: $C_{20}H_8Br_8O_3$ (935.55) Calculated: C 25.68%, H 0.86%, Br 68.33%, O 5.13%. Found: C 25.81%, H 0.74%, Br 68.51%, O 5.22%.

EXAMPLE 3

Preparation of
p-(2.4.6-trichlorophenoxymethyl)-benzoic acid-(pentabromophenyl) ester:

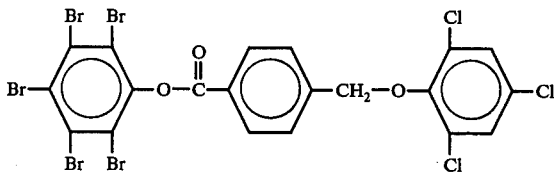

In a four-liter three-necked flask equipped with stirrer, reflux condenser and thermometer, 16 g (= 0.4 mole) of solid sodium hydroxide was dissolved in two liters of methyl glycol at 60° C and then 79 g (= 0.4 mole) of trichlorophenol was stirred in, and then 256.5 g (= 0.4 mole) of p-chloromethylbenzoic acid pentabromophenyl ester was added. The reaction mixture was brought to ebullition and reluxed for one hour, with stirring.

Beginning at an internal temperature of 115° C, a white, voluminous precipitate formed, which increased in quantity as refluxing proceeded. At the end of the reaction time, the contents of the flask were cooled to room temperature and the solids were suction filtered. The filter cake was processed as described in Example 1 and yielded, after drying at 110° C, 302 grams of ether ester, corresponding to 94% of the theoretically possible amount. Melting point of the raw product: 190°-194° C.

10 grams, recrystallized from 450 ml of methyl glycol, yielded 7.4 grams of a crystallizate melting at 193°-195° C.

Elemental Analysis: $C_{20}H_8Br_5Cl_3O_3$ (802.19) Calculated: C 29.95%, H 1.00%, O 5.97%, Br 49.81%, Cl 13.26% Found: C 29.82%, H 0.92%, O 5.82%, Br 50.02%, Cl 12.98%

EXAMPLE 4

Preparation of
p-(2,3,4,6-tetrachlorophenoxymethyl)-benzoic acid-(pentabromophenyl) ester:

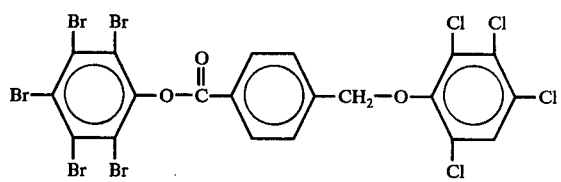

By the procedure described in Example 3,
1.3 liters of methyl glycol (B.P. 122°-126° C),
12 g (= 0.3 mole) of sodium hydroxide
69.6 g (= 0.3 mole) of 2,3,4,6-tetrachlorophenol and
192.4 g (= 0.3 mole) of p-chloromethylbenzoic acid (pentabromophenyl) ester were reacted by refluxing for one hour. The ether ester of the above formula precipitated at the ebullition temperature in the form of a white, voluminous precipitate. Processing was performed as described in Example 1. 228 grams of raw ether ester, corresponding to a 91% yield were obtained, melting point 231°-241° C. 10 grams, upon recrystallization from 50 ml of dibromoethane, yielded crystals melting at 241°-244° C.

Elemental Analysis: $C_{20}H_7Br_5Cl_4O_3$ (836.64) Calculated: C 28.71%, H 0.84%, O 5.75%, Br 47.75%, Cl 16.95% Found: C 28.56%, H 0.83%, O 5.60%, Br 47.93%, Cl 16.8%

EXAMPLE 5

Preparation of o-(pentachlorophenoxymethyl)-benzoic acid-(pentabromophenyl) ester In a four-liter three-necked flask,
3 liters of methyl glycol,
12 grams (= 0.3 mole) of sodium hydroxide,
192.4 grams (= 0.3 mole) of o-chloromethylbenzoic acid-pentabromophenyl ester were reacted as in Example 1.

211 g (= 81% yield) was obtained of the ether ester which melted at 227°-230° C. An additional 19.5 g of melting point 224°-228° C was obtained from the methyl glycol mother liquor. Upon recrystallization the melting point was 231°-233° C.

Elemental analysis: $C_{20}H_6Br_5Cl_5O_3$ (871.08) Calculated: C 27.58%, H 0.69%, O 5.51%, Br 45.87%, Cl 20.35% Found: C 27.77%, H 0.68%, O 5.38%, Br 45.6%, Cl 20.14%

EXAMPLE 6

Preparation of p-(2,4,6-tribromophenoxymethyl)-benzoic acid-(pentachlorophenyl) ester As described in Example 5,
2 liters of methyl glycol, B.P. 122°–126° C,
14 g (= 0.35 mole) of sodium hydroxide,
115.8 g (= 0.35 mole) of tribromophenol, and
146.7 g (= 0.35 mole) of p-chloromethylbenzoic acid pentachlorophenyl ester
were reacted.

The ether ester formed beginning at 90° C and precipitated as a white, voluminous precipitate. Yield 207 g = 83%). M.P. 225°–231° C; after recrystallization: 230°–232° C.

Elemental analysis: $C_{20}H_8Br_3Cl_5O_3$ (713.28). Calculated: C 33.68%, H 1.13%, O 6.73%, Br 33.61% Cl 24.87% Found: C 33.81%, H 1.20%, O 6.75%, Br 33.3%, Cl 24.98%

EXAMPLE 7

Preparation of o-(pentabromophenoxymethyl)-benzoic acid(2,4,6-tribromophenyl)-ester

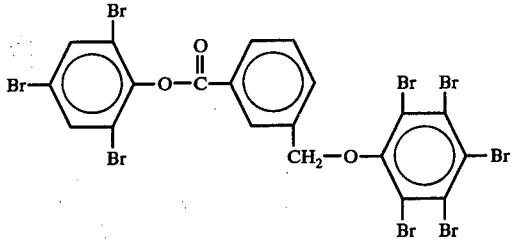

2.5 liters of methyl glycol,
16 g (= 0.4 mole) of sodium hydroxide
195.5 g (= 0.4 mole) of pentabromophenol, and
193.4 g (= 0.4 mole) of o-chloromethylbenzoic acid tribromophenyl ester
were reacted as described in Example 5.

At 70° C a clear solution formed, and, beginning at 105° C, a white, very voluminous precipitate formed.

After working up and drying, 331 g (= 88.5%) of product was obtained. The melting point was 277°–279° C, and after recrystallization from 400 ml of xylene it was 279°–281° C.

Elemental analysis: $C_{20}H_8Br_8O_3$ (935.55). Calculated: C 25.67%, H 0.86%, O 5.13%, Br 68.33%. Found: C 25.84%, H 0.78%, O 4.98%, Br 68.3%

EXAMPLE 8

Preparation of o-(2,4,6-tribromophenoxymethyl)-benzoic acid(2,4,6tribromophenyl) ester (a) By the "one-vessel method" from o-chloromethylbenzoyl chloride without isolation of the o-chloromethylbenzoic acid tribromophenyl ester:

In a 500-ml flask equipped with stirrer, dropping funnel, reflux condenser and thermometer, 8 g (= 0.2 mole) of sodium hydroxide was dissolved at 60° C in 100 ml of methyl glycol, then 66.2 g (= 0.2 mole) of tribromophenol was added, and 18.9 g (= 0.1 mole) of o-chloromethylbenzoyl chloride was added drop by drop to the clear phenolate solution, after the latter had been cooled to 35° C, this being carried out over a period of 45 minutes with thorough stirring. Sodium chloride precipitated.

Then the mixture was refluxed for 1 hour and cooled, whereupon the ether ester crystallized out. After the product had been suction filtered, washed with water and vacuum dried at 80° C, 64.5 g (= 82.6%) of the nearly pure ether ester was obtained, which melted at 170°–173.5° C.

Calculated: C 30.88%, H 1.29%, O 6.18%, Br 61.65%. Found: C 31.01%, H 1.20%, O 6.11%, Br 61.48%.

(b) From o-chloromethylbenzoic acid-(2,4,6-tribromophenyl)-ester:

In a one-liter three-necked flask,
500 ml of methyl glycol,
16 g (= 0.4 mole) of sodium hydroxide,
132.4 g (= 0.4 mole) of tribromophenol, and
193.4 g (= 0.4 mole of o-chloromethylbenzoic acid tribromophenyl ester were reacted as in Example 1. Upon cooling, the ether ester began to precipitate in crystals at 100° C. At room temperature they were suction filtered, washed chloride-free with water, and dried in vacuo at 100° C. Yield: 264 g (= 85%) with a crude melting point of 170°–173° C.

(c) Preparation and isolation of o-chloromethylbenzoic acid-2,4,6-tribromophenyl)-ester:

In a two-liter three-necked flask, 40 g of sodium hydroxide was dissolved in 950 ml of methyl glycol at 60° C, and then 331 g (= 1 mole) of tribromophenol was stirred in, and then 189 g (= 1 mole) of o-chloromethyl benzoyl chloride was added, drop by drop, with stirring, over a period of 1¾ hours, at a reaction mixture temperature not exceeding 40° C, into the clear phenolate solution, cooled to 30° to 40° C. Stirring was then continued for one hour at room temperature; the mixture was then cooled to 0° C, the crystallizate was suction filtered and washed free of sodium chloride with water, and dried at 80° C in a vacuum drying chamber. 397 g (= 82% yield) was obtained of o-chloromethylbenzoic acid tribromophenyl ester melting at 180°–110° C.

EXAMPLE 9

Preparation of o-(pentabromphenoxymethyl)-benzoic acid-(pentabromophenyl) ester (a) o-chloromethylbenzoic acid pentabromophenyl ester:

In a 500-ml three-necked flask, 4 g (= 0.1 mole) of sodium hydroxide was dissolved at 60° C in 270 ml of methyl glycol, and 48.9 g of pentabromophenol was stirred in for the preparation of a phenolate solution, as in Example 8c. At 30° to 34° C, 18.9 g (— 0.1 mole) of o-chloromethylbenzoyl chloride was added drop by drop, with stirring, over a period of about 40 minutes, whereupon a white, crystalline preciptate settled out, which after 1 hour was suction filtered. After the product had been stirred up in water, suction filtered, washed and dried, 58 g (= 90.5%) of o-chloromethylbenzoic acid pentabromophenyl ester was obtained, which melted at 201°–205° C.

(b) By the "one-vessel method", directly from o-chloromethylbenzoyl chloride:

In a 6-liter flask, 32 g of sodium hydroxide was dissolved at 60° C in 4 liters of methyl glycol, and then 391 g (= 0.8 mol) of pentabromophenol were dissolved whereupon this phenolate solution was cooled to 35° C. At this temperature 75.7 g of o-chloromethyl benzoyl chloride was added, drop by drop, with stirring, over a period of 50 minutes. The ester precipitated in crystal form.

Then the mixture was heated for 5 hours at ebullition, and then cooled and worked up as in the preceding examples.

Product: 353 g (= 80.7% yield) M.P. 259°–263° C.

(c) From o-chloromethyl benzoic acid pentabromophenyl ester:

In a two-liter flask, 5.6 of potassium hydroxide was dissolved at 75° C in 800 ml of methyl glycol; then 48.9 g (= 0.1 mole) of pentabromphenol was stirred in. To this phenolate solution, at 75° C, 64.15 g was added of the o-chloromethylbenzoic acid pentabromophenyl ester, prepared as in Example 9a, and the mixture was heated with stirring to ebullition. It was refluxed for an hour, then cooled, and the solids were isolated and worked up as described in the preceding examples.

Product: 90 g of ether ester (= 82%), M.P. 256° to 261° C. After recrystallization, M.P. 262°–263.5%. Elemental Analysis: $C_{20}H_6Br_{10}O_3$ (1093.36). Calculated: C 21.97%, H 0.55%, O 4.39%, Br 73.09% Found: C 22.11%, H 0.62%, O 4.57%, Br 72.90%.

EXAMPLE 10

Preparation of p-(pentabromphenoxymethyl)-benzoic acid-(pentabromophenyl) ester.

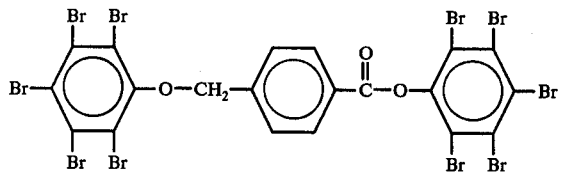

(a) The following were brought to reaction in the four-liter three-necked flask as in Example 1:
2 liters of methyl glycol.
8 g (= 0.2 mole) of sodium hydroxide,
97.75 g (= 0.2 mole) of pentabromophenol, and
128.25 g (= 0.2 mole) of p-chloromethylbenzoic acid-pentabromophenyl ester.

The precipitate which formed after one hour of refluxing was suction filtered at room temperature, washed with water until free of chloride, and dried. 189.2 g (86%) of ether ester was obtained, melting point 292°–296° C. Upon recrystallization from xylene, the melting point was 294°–296.5° C.

Elemental Analysis: $C_{20}H_6Br_{10}O_3$ (1093.36). Calculated: C 21.97%, H 0.55%, O 4.39%, Br 73.09%. Found: C 21.82%, H 0.47%, O 4.27%, Br 72.86%.

(b) By the "one-vessel process" from p-chloromethylbenzoyl chloride, the same procedure as that of Example 9b yielded the same ether ester as obtained under (a). 93 g (yield 85%) was obtained, melting point 294°–289° C.

EXAMPLE 11

Preparation of p-(2,4,6-tribromophenoxymethyl)-benzoic acid(2,4,6-tribromophenyl)-ester:

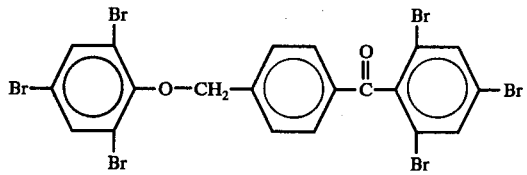

(a) From p-chloromethylbenzoic acid tribromphenyl ester:

The following were reacted in a 500-ml flask in the manner described in Example 1:
200 ml of methyl glycol,
4.0 g (= 0.1 mole) of sodium hydroxide,
33.1 g (= 0.1 mole) of tribromophenol, and
48.4 g (= 0.1 mole) of p-chloromethylbenzoic acid-tribromophenyl ester.

The ether ester precipitated when ebullition began, in the form of a crystalline, colorless precipitate, which was isolated as described in Example 1. Yield: 70.8 g (91.2%), M.P. 182°–184° C; after recrystallization, M.P. 183°–184.5° C.

Elemental Analysis: $C_{20}H_{10}Br_6O_3$ (777.75). Calculated: C 30.89%, H 1.30%, O 6.17%, Br 61.64%. Found: C 31.04%, H 1.41%, O 6.08%, Br 61.4%.

(b) Directly from p-chloromethylbenzoyl chloride:
As described in Example 10b, we reacted:
2.5 liters of methyl glycol,
160 g (= 4 moles) of sodium hydroxide,
1324 g (= 4 moles) of tribromophenol, and
379 g (= 2 moles) of 99.0% p-chloromethylbenzoyl chloride.

To complete the reaction the mixture was refluxed for 6 hours. Upon cooling, the reaction mixture solidified to a crystalline mass. Yield of ether ester: 1180 g (76% yield) melting at 179°–183° C.

EXAMPLE 12

Preparation of o-(pentachlorophenylmercaptomethyl)-benzoic acid-(pentabromophenyl) ester

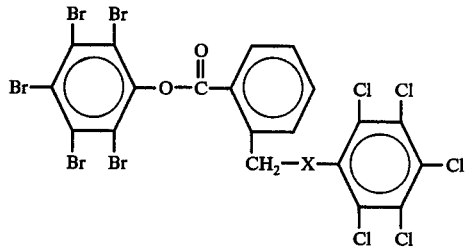

By the procedure described in Example 1, the following were reacted in a two-liter three-necked flask:
1 liter of methyl glycol,
12 g (= 0.3 mole) of sodium hydroxide,
84.75 g (= 0.3 mole) of pentachlorothiophenol and
192.4 g (= 0.3 mole) of o-chloromethylbenzoic acid-pentabromophenyl ester.

Yield of thioether ester: 221 g (= 83%), M.P. 175°–181° C; after recrystallization: 185°–187° C. Elemental Analysis: $C_{20}H_6Br_5Cl_5O_2S$ (887.14) Calculated: C 27.08%, H 0.68%, O 3.61%, Br 45.03%, Cl 19.98% S 3.61%. Found: C 27.21%, H 0.59%, O 3.45%, Br 45.3%, Cl 19.7% S 3.54%.

EXAMPLE 13

Preparation of o-(pentachlorophenylmercaptomethyl)-benzoic acid-(2,4,6-tribromophenyl) ester

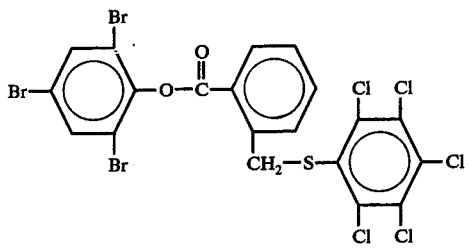

In a one-liter three-necked flask the following were reacted as described in Example 1:
500 ml of methyl glycol
19.6 g (= 0.35 mole) of potassium hydroxide,
98.85 g (= 0.35 mole) of pentachlorothiophenol and
169.2 g (= 0.35 mole) of o-chloromethylbenzoic acid-tribromophenyl ester.

The reaction began at 70° C, and the mixture was refluxed to complete the reaction for 1½ hours.

Yield: 224.5 g (= 88%) of crude thioether ester, melting point 194°-201° C; after recrystallization, M.P. 202°-204° C.

Elemental Analysis: $C_{20}H_8Br_3Cl_5O_2S$ (729.34) Calculated: C 32.94%, H 1.10%, O 4.40%, Br 32.87%, Cl 24.30% S 4.39%. Found: C 33.12%, H 0.98%, O 4.28%, Br 33.1%, Cl 24.13% S 4.25%.

EXAMPLE 14

Preparation of p-(pentachlorophenylmercaptomethyl)-benzoic acid-(2,4,6-tribromophenyl) ester The following were reacted in a 100-ml flask as described on Example 1:
20 ml of methyl glycol,
0.8 g (= 0.02 mole) of sodium hydroxide,
5.65 g (= 0.02 mole) of pentachlorotiophenol and
9.67 g (= 0.02 mole) of p-chloromethylbenzoic acid-tribromophenyl ester.

The product was 10.8 g (= 74% yield) of p-thioether ester M.P. 180°-183° C; after recrystallization, M.P. 183.5°-185.5° C.

Elemental Analysis: $C_{20}H_8Br_3Cl_5O_2S$ (729.34) Calculated: C 32.94%, H 1.10%, O 4.40%, Br 32.87%, Cl 24.30% S 4.39% Found: C 33.16%, H 0.97%, O 4.39%, Br 33.1%, Cl 24.1% S 4.28%

EXAMPLE 15

Preparation of p-(pentachlorophenylmercaptomethyl)-benzoic acid pentabromophenyl ester The following substances were used as in the foregoing examples:
40 ml of methyl glycol
0.8 g of sodium hydroxide
5.65 g of pentachlorothiophenol and
12.82 g (= 0.02 mole) of p-chloromethylbenzoic acid pentabromophenyl ester.

The performance of the reaction and the working up of the product were as described in Example 1. The product was 15.8 g (= 89% yield) of the above thioether ester having a melting point of 241°-248° C. This was recrystallized from 125 ml of xylene, and the melting point was then 251°-253° C.

Elemental Analysis: $C_{20}H_6Br_5Cl_5O_2S$ Calculated: C 27.08%, H 0.68%, O 3.61%, Br 45.03%. Cl 19.98%, S 3.61%. Found: C 27.08%, H 0.70%, O 3.82%, Br 45.34%, Cl 20.1%, S 3.28%.

EXAMPLE 16

Preparation of p-(pentabromophenoxymethyl)-thiobenzoic acid-S-(pentachlorophenyl) ester

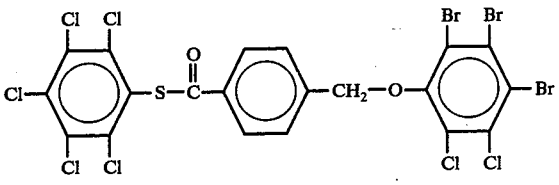

In the manner described above, the following were reacted:
50 ml of methyl glycol, B.P. 122°-126° C
0.6 g (= 0.015 mole) of sodium hydroxide,
7.33 g (= 0.015 mole) of pentabromophenol and
6.52 g (= 0.015 mole) of p-chloromethylthiobenzoic acid-S-(pentachlorophenyl ester).

5.8 g (= 43.5% yield) of ether thioester melting at 229°-236° C was obtained. When we recrystallized this from 25 ml of xylene we obtained crystals melting at 243°-245° C.

Elemental Analysis: $C_{20}H_6Br_5Cl_5O_2S$ Calculated: C 27.08%, H 0.68%, O 3.61%, Br 45.03%, Cl 19.98%, S 3.61%. Found: C 27.21%, H 0.55%, O 3.49%, Br 45.24%, Cl 20.13%, S 3.68%.

EXAMPLE 17

Preparation of 2,2-diphenylpropane-bis-4,4'-[p-(2,4,6-tribromophenoxymethyl)-benzoic acid)] ester

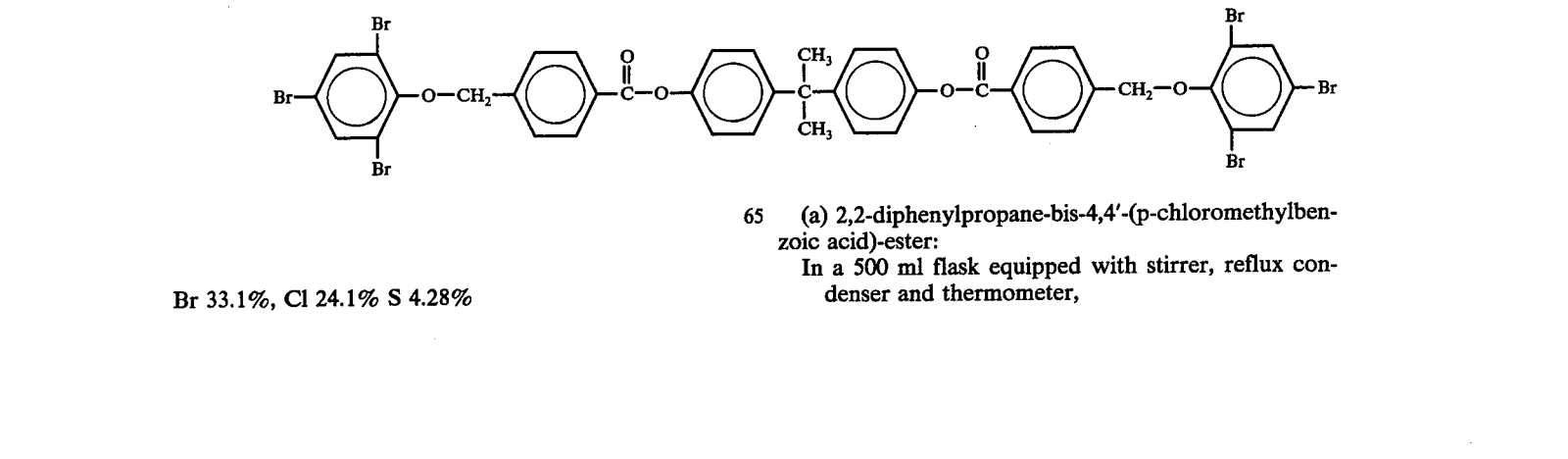

(a) 2,2-diphenylpropane-bis-4,4'-(p-chloromethylbenzoic acid)-ester:

In a 500 ml flask equipped with stirrer, reflux condenser and thermometer, 300 ml of dry xylene,
114.2 g (= 0.5 mole) of 4,4'-dihydroxy-(2,2-diphenyl-propane) = Bisphenol A,
189.2 g (= 1.0 mole) of 99.3% p-chloromethylbenzoyl chloride, and
0.5 ml of absolute pyridine are combined and slowly heated, with stirring. At 100° C a clear solution developed, and a strong evolution of hydrogen chloride. The reaction temperature was maintained for 30 minutes at 100° to 110° C, and then increased to the boiling temperature. To complete the reaction, the mixture was refluxed for 5½ hours. Upon cooling, colorless, needle-shaped crystals separated from the light yellow, clear reaction mixture, and these were suction filtered at 0° C.

103 g (77.3% yield) of p-chloromethylbenzoic acid ester was obtained, which melted at 142° to 145° C; upon recrystallization, the melting point was 150° to 152° C. An additional 30 grams could be obtained by concentrating the mother liquor, so that virtually quantitative yield was obtained.

(b) Preparation of the bisether bisester:
By the procedure of Example 1, the following were reacted:
450 ml of methyl glycol, B.P. 122° to 126° C
15.2 g (= 0.38 mole) of sodium hydroxide,
125.75 g (= 0.38 mole) of tribromophenol, and
101.4 g (= 0.19 mole) of bis-(chloromethyl) compound prepared as in (a).

During the heating, at 110° C a clear reaction solution was obtained, from which sodium chloride precipitated at the refluxing temperature. Refluxing was performed for one hour.

Upon cooling to room temperature, the reaction product precipitated. After suction filtering, washing and drying at 80° C, the yield was 165 g (77%), M.P. 126° to 135° C.

After recrystallization the melting point was 145°-146° C.

Elemental Analysis: C₄₃H₃₀Br₆O₆ (1122.17). Calculated: C 46.03%, H 2.69%, O 8.55%, Br 42.73%. Found: C 46.24%, H 2.70%, O 8.28%, Br 42.95%.

EXAMPLE 18

Preparation of (3,3',5,5'-tetrabromo-2.2-diphenylpropane)-4,4'-bis-[p-(2,4,6-tribromophenoxymethyl)-benzoic acid)] ester:

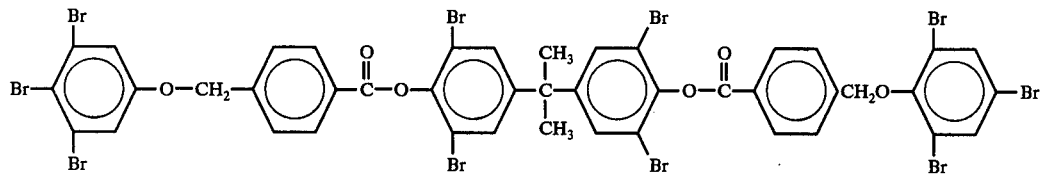

(a) (3,3',5,5'-Tetrabromo-2,2-diphenylpropane)-4,4'-bis-(p-chloromethylbenzoic acid ester):
In the manner described in Example 17a,
150 ml of dry xylene,
108.8 g (= 0.2 mole) of tetrabromo-bisphenol A,
75.7 g (= 0.4 mole) of 99.3% p-chloromethylbenzoyl chloride, and
0.2 ml of absolute pyridine
were heated, with stirring, in a 500 ml flask. A clear solution formed at 100° C. The formation of hydrogen chloride began at the boiling temperature. The solution was refluxed for 22 hours, the orange-colored solution was greatly concentrated in the rotary vacuum evaporator, the bis-chloromethyl compound precipitating mostly as a colorless crystallizate. This was suction filtered and dried in vacuo at 120° C. The product was 153 g (90.6% yield), M.P. 193°-199° C; upon recrystallization, M.P. 202°-205° C.

(b) Preparation of the bisether bisester:
700 ml of methyl glycol,
9.6 g (= 0.24 mole) of sodium hydroxide,
79.4 g (= 0.24 mole) of tribromophenol, and
101.9 g (= 0.12 mole) of the bis-chloromethyl compound prepared as described under (a) were reacted as described under Example 1. At the boiling temperature of the mixture a virtually clear solution formed from which a colorless precipitate settled after about 20 minutes of boiling. The mixture was refluxed for a total of 1½ hours. After processing in the usual manner, the product was 159 g (92% yield) of bisether bisester melting at 208° to 215° C; upon recrystallization twice from xylene, the melting point was 240°-242° C.

Elemental Analysis: C₄₃H₂₆Br₁₀O₆ (1437.77) Calculated: C 35.92%, H 1.82%, O 6.68%, Br 55.58%. Found: C 36.11%, H 1.78%, O 6.56%, Br 55.4%. EXAMPLE 19

Preparation of 2,2-diphenylpropane-bis-4,4'-[o-(2,4,6-tribromophenoxymethyl)-benzoic acid)] ester The compound is the same as that of Example 17, but first o-chloromethyl benzoyl chloride was reacted with bisphenol A.

By a procedure similar to that of Example 1, the following were reacted in the one-liter three-necked flask:
500 ml of methyl glycol
13.6 g (= 0.34 mole) of sodium hydroxide,
112.5 g (= 0.34 mole) of tribromophenol, and
90.7 g (= 0.17 mole) of 2,2-diphenylpropane-bis-4,4'-(o-chloromethylbenzoic acid) ester.
Beginning at 80° C a clear, dissolved, homogeneous reaction mixture was obtained, which was refluxed for 1 hour. Sodium chloride began to precipitate at 100° C. When the reaction mixture cooled, a microcrystalline precipitate settled out beginning at about 60° C.

Yield: 139.5 g (= 73% yield) of bisether bisester of a melting point of 127° to 133° C; upon recrystallization, the melting point was 148° to 149.5° C.

Elemental Analysis: C₄₃H₃₀Br₆O₆ (1122.17). Calculated: C 46.03%, H 2.69%, Br 42.73%, O 8.55% Found: C 46.25%, H 2.70%, Br 42.52%, O 8.23%

EXAMPLE 20

Preparation of (3,3',5,5'-tetrabromo-2,2-diphenylpropane)-4,4'-bis-[o-(2,4,6-tribromophenoxymethyl)-benzoic acid)] ester This o-compound corresponding to Example 18 was prepared precisely like the p-compound of Example 18b, from the following components:

300 ml of methyl glycol,
7.44 g (= 0.186 mole) of sodium hydroxide,
61.55 g (= 0.186 mole) of tribromphenol and
79 g (= 0.093 mole) of (3,3',5,5'-tetrabromo-2,2-diphenylpropane)-4,4'-bis-(o-chloromethylbenzoic acid ester).

A clear solution formed at 100° C, and sodium chloride precipitated beginning at 105° C. The mixture was refluxed for one hour, the reaction product remaining in solution. It was cooled down to room temperture with stirring, and worked up as previously described. The yield was 94 g (= 70,5%), the melting point 120°-130° C; after recrystallization twice from methyl glycol, M.P. 138°-141° C.

Elemental Analysis: $C_{43}H_{26}Br_{10}O_6$ (1437.77). Calculated: C 35.92%, H 1.82%, Br 55.58%, O 6.68% Found: C 36.13%, H 1.94%, Br 55.2%, O 6.42%.

EXAMPLE 21

Preparation of 4,4'-dihydroxydiphenylsulfone-bis-0,0-[p-(pentabromophenoxymethyl)-benzoic acid] ester

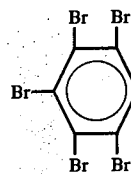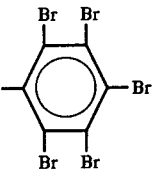

By the method of Example 1 we reacted the following:
1.25 liters of methyl glycol, B.P. 122°-126° C,
16 g (= 0.4 mole) of sodium hydroxide,
195.5 g (= 0.4 mole) of pentabromophenol and
88.9 g (= 0.2 mole) of 4,4'-dihydroxydiphenylsulfone-bis-0,0-(p-chloromethylbenzoic acid) ester.

A clear reaction solution formed at 100° C. Beginning at 110° C, a virtually colorless, crystalline precipitate formed. Refluxing was performed for 2 hours.

Yield 243 g (= 83.2%) of bisether bisester, M.P. 245°-252° C; when recrystallized from 1,2-dibromoethane, M.P. 261°-263° C.

Elemental Analysis: $C_{40}H_{20}Br_{10}O_8S$ (1459.76). Calculated: C 32.91%, H 1.38%, O 8.77%, S 2.20%, Br 54.74%. Found: C 33.14%, H 1.54%, O 8.62%, S 2.41%, Br 54.54%.

EXAMPLE 22

Preparation of 4,4'-dihydroxydiphenylsulfone-bis-0,0-[2-(pentabromophenoxymethyl)-benzoic acid] ester:

(a) Preparation of 4,4'-dihydroxydiphenylsulfone-bis-0,0-(2-chloromethylbenzoic acid) ester:

In a 500 ml four-necked round flask, 50.5 g (= 0.2 mole) of 4,4'-sulfonyldiphenol was dissolved in 300 ml of anhydrous tetrahydrofuran with the exclusion of moisture, and this solution was mixed with 40.5 g = 55.2 ml (= 0.4 mole) of anhydrous triethylamine. With self-heating up to about 33° C, the formation of salt began, with the formation of a precipitate. The contents of the flask was raised to 50° C with stirring, and then 75.57 g (= 0.4 mole) of 2-chloromethylbenzoyl chloride was added drop by drop over a period of one hour. The reaction mixture warmed by itself to 58° C, while at the same time a further settling of a fine precipitate took place.

To complete the reaction, the mixture was stirred for another hour at 60° C, and then the mixture was cooled to room temperature and stirred into 1.4 liters of cold water. The precipitate was suction filtered and washed free of chloride with water, whereupon the product was dried at 80° C in the circulating air drying oven. The yield was 97.5 g (= 87.7%) of bis-chloromethyl compound melting at 121°-127° C; after two recrystallizations from a 1:1 mixture of acetone and methanol the melting point was 133°-134.5° C.

Elemental Analysis: $C_{28}H_{20}O_6Cl_2S$ (555.44). Calculated: C 60.55%, H 3.60%, O 17.30%, Cl 12.78%, S 5.77%. Found: C 60.71%, H 3.69%, O 17.27%, Cl 12.57%, S 5.81%.

(b) Preparation of the bisether bisester:

In the manner described in Example 1, the following were reacted in a one-liter three-necked round flask and worked up:
600 ml of methyl glycol,
4 g (= 0.1 mole) of sodium hydroxide,
48.9 g (= 0.1 mole) of pentabromophenol, and
27.8 g (= 0.05 mole) of the bis-chloromethyl compound prepared as described under a). At 80° C a clear solution was formed; beginning at 110° C, a voluminous, colorless precipitate was formed. Yield 46 g (= 63%) melting point 248°-253° C; upon recrystallization, melting point 261°-263° C.

Elemental Analysis: $C_{40}H_{20}Br_{10}O_8S$ (1459.76). Calculated: C 32.91%, H 1.38%, Br 54.74%, O 8.77%, S 2.20%. Found: C 32.99%, H 1.32%, Br 54.5%, O 8.64%, S 2.24%.

EXAMPLE 23

The following table gives the results of measurements of the flameproofing action of substances of the invention on plastics.

The values listed under "LOI-% $O_2$" were determined in accordance with ASTM D 2863-70. They represent the oxygen concentration, expressed in the percent by volume of a mixture of oxygen and nitrogen which just sustains the combustion of the specimen. The higher the oxygen index is, the better is the flame inhibiting action of the formulation.

The fire-retardant was incorporated by means of a roller mixer. The roll skins obtained were then pressed to form the test strips.

The following tabulated comparison clearly shows the superiority of many substances of the invention over known fire-retardants which have proven to have good effectiveness.

TABLE

PE = polyethylene, PP = polypropylene, PS = polystyrene
* = per 100 g of plastic

| Plastic | Substance of Example | Avg. amt. of fire retardant ether ester | $Sb_2O_3$ | LOI Vol.% $O_2$ |
|---|---|---|---|---|
| PE | — | 0 | 0 | 17.3 |

TABLE-continued

PE = polyethylene, PP = polypropylene, PS = polystyrene
* = per 100 g of plastic

| Plastic | Substance of Example | Avg. amt. of fire retardant ether ester | $Sb_2O_3$ | LOI Vol.% $O_2$ |
|---|---|---|---|---|
| PE | Octabromodiphenyl ether | 9 g | 4 g | 27.2 |
| PE | Octabromodiphenyl | 12 g | 4 g | 27.3 |
| PE | Octabromodiphenyl | 12 g | 2 g | 26.4 |
| PE | Octabromodiphenyl | 9 g | 4 g | 27.3 |
| PE | Octabromodiphenyl | 9 g | 2 g | 26.3 |
| PE | Octabromodiphenyl | 6 g | 4 g | 26.9 |
| PE | Octabromodiphenyl | 6 g | 2 g | 26.0 |
| PE | 1 | 12 g | 4 g | 28.3 |
| PE | 1 | 12 g | 2 g | 27.9 |
| PE | 1 | 9 g | 4 g | 27.9 |
| PE | 1 | 6 g | 3 g | 26.7 |
| PE | 7 | 12 g | 4 g | 28.4 |
| PE | 7 | 12 g | 2 g | 28.4 |
| PE | 7 | 6 g | 2 g | 26.3 |
| PE | 8 a | 12 g | 4 g | 28.4 |
| PE | 8 a | 12 g | 2 g | 28.2 |
| PE | 8 a | 9 g | 2 g | 27.4 |
| PE | 9 b | 12 g | 2 g | 27.7 |
| PE | 9 b | 9 g | 4 g | 28.0 |
| PE | 9 b | 6 g | 2 g | 26.8 |
| PE | 10 b | 12 g | 4 g | 27.8 |
| PE | 10 b | 9 g | 2 g | 26.4 |
| PE | 11 b | 12 g | 4 g | 28.2 |
| PE | 11 b | 9 g | 2 g | 27.4 |
| PE | 12 | 12 g | 4 g | 28.0 |
| PE | 12 | 12 g | 2 g | 27.7 |
| PE | 12 | 9 g | 4 g | 28.0 |
| PE | 12 | 6 g | 3 g | 26.9 |
| PE | 12 | 6 g | 2 g | 26.2 |
| PE | 13 | 12 g | 2 g | 27.2 |
| PE | 13 | 9 g | 2 g | 26.9 |
| PE | 17 | 9 g | 2 g | 26.4 |
| PE | 19 | 12 g | 2 g | 26.7 |
| PE | 19 | 9 g | 4 g | 26.7 |
| PE | 20 | 12 g | 4 g | 28.6 |
| PE | 20 | 9 g | 4 g | 28.2 |
| PE | 20 | 9 g | 2 g | 27.3 |
| PP | — | 0 | 0 | 17.3 |
| PP | Octabromodiphenyl ether | 10 g | 4 g | 23.8 |
| PP | Octabromodiphenyl ether | 9 g | 4 g | 23.7 |
| PP | 12 | 9 g | 4 g | 24.2 |
| PP | 20 | 12 g | 4 g | 26.2 |
| PP | 20 | 9 g | 4 g | 26.1 |
| PS | — | 0 | 0 | 17.1 |
| PS | Decarbromodiphenyl ether | 12 g | 5 g | 23.3 |
| PS | Decarbromodiphenyl ether | 9 g | 4 g | 22.7 |
| PS | Decabromodiphenyl ether | 6 g | 4 g | 21.1 |
| PS | Octabromodiphenyl ether | 9 g | 4 g | 22.0 |
| PS | 1 | 12 g | 5 g | 24.3 |
| PS | 1 | 9 g | 4 g | 23.0 |
| PS | 9 b | 12 g | 6 g | 23.3 |
| PS | 10 b | 12 g | 6 g | 23.4 |
| PS | 21 | 12 g | 6 g | 23.7 |
| PS | 22 | 12 g | 6 g | 22.7 |

What is claimed is:

1. Aryloxymethylbenzoic acid phenyl ester of the formula

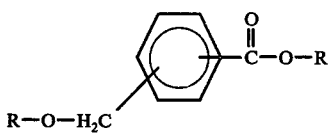

wherein each R represents the residue of a mononuclear phenol substituted by at least one of chlorine and bromine.

2. Ester of claim 1, wherein each R substituted by at least two of said halogen residues.

3. Ester of claim 1, wherein each R is substituted by at least three of said halogen residues.

4. Ester of claim 1, wherein each R is substituted by bromine and the bromine content of the ester is 40 to 50 wt.% of the ester.

5. Plastic composition containing the ester of claim 1 in an amount effective to render the composition fire resistant.

6. Plastic composition containing the ester of claim 2 in an amount effective to render the composition fire resistant.

7. Plastic composition containing the ester of claim 3 in an amount effective to render the composition fire resistant.

8. Plastic composition containing the ester of claim 4 in an amount effective to render the composition fire resistant.

9. Aryloxymethylbenzoic acid phenyl ester of the formula

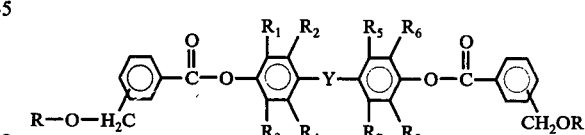

wherein:
   each R represents the residue of a mononuclear phenol substituted by at least one of chlorine and bromine,
   Y is nothing, a methylene group, a dialkylmethylene group, a chalcogen atom, -SO-, or a sulfone group, and
   each of $R_1$ to $R_8$ represents hydrogen or halogen.

10. Ester of claim 9, wherein Y is a dialkylmethylene group.

11. Plastic composition containing the ester of claim 9 in an amount effective to render the composition fire resistant.

12. Plastic composition containing the ester of claim 10 in an amount effective to render the composition fire resistant.

* * * * *

UNITED STATES PATENT AND TRADEMARK OFFICE
CERTIFICATE OF CORRECTION

PATENT NO. : 4,105,628
DATED : August 8, 1978
INVENTOR(S) : Egon Norbert Petersen It is certified that error appears in the above-identified patent and that said Letters Patent are hereby corrected as shown below:

Col. 1, line 21, change "isometric" to --isomeric--;

Col. 9, line 15, after "5.6" insert --g--.

Signed and Sealed this

Eighth Day of May 1979

[SEAL]

Attest:

RUTH C. MASON
Attesting Officer

DONALD W. BANNER
Commissioner of Patents and Trademarks